US00PP37410P2

(12) United States Plant Patent
Giesen

(10) Patent No.: US PP37,410 P2
(45) Date of Patent: May 5, 2026

(54) ***PETUNIA* PLANT NAMED 'PEHY0089'**

(50) Latin Name: *Petunia hybrida*
Varietal Denomination: PEHY0089

(71) Applicant: SYNGENTA CROP PROTECTION AG, Basel (CH)

(72) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/228,938

(22) Filed: Jun. 5, 2025

(51) Int. Cl.
*A01H 5/02* (2018.01)
*A01H 6/82* (2018.01)

(52) U.S. Cl.
USPC ..... Plt./356.1

(58) Field of Classification Search
USPC ..... Plt./356.1
See application file for complete search history.

*Primary Examiner* — Susan McCormick Ewoldt
(74) *Attorney, Agent, or Firm* — Dale Skalla

(57) ABSTRACT

A new *Petunia* plant named 'PEHY0089' particularly distinguished by its medium sized, dark black with dark purple center flowers, very early flowering and mounding plant habit.

1 Drawing Sheet

Name of the genus and species of the plant claimed: *Petunia hybrida.*

Varietal denomination: 'PEHY0089'.

BACKGROUND OF THE NEW PLANT

The present invention comprises a new *Petunia*, botanically known as *Petunia hybrida*, and hereinafter referred to by the variety name 'PEHY0089'.

'PEHY0089' is a product of a planned breeding program. The new cultivar has a medium sized flowers with an intense dark black flower color, early flowering and has a mounding plant habit.

'PEHY0089' originated from a hybridization made in October 2019 in a controlled breeding environment in Gilroy California. The female parent was the proprietary selection 'BB1411-1V' (not patented in US). Compared to 'PEHY0089', it has a bit more trailing plant habit, has a purplish black flower color, is later flowering and has a bit larger flower.

The male parent of 'PEHY0089' was the unpatented proprietary selection 'BB0145-2V'. 'BB0145-2V' is a plant with a bit larger flowers, later flowering, a more trailing plant habit, and with a blue flower color.

The resulting seeds were sown in January 2020. 'PEHY0089' was selected as one flowering plant within the progeny of the stated cross in May 2020 in a controlled environment in Gilroy California.

The first act of asexual reproduction of 'PEHY0089' was accomplished when vegetative stem cuttings were propagated from the initial selection in June 2020 in a controlled environment in Gilroy California.

BRIEF SUMMARY OF INVENTION

Horticultural examination of plants grown from cuttings of the plant initiated in June 2020 and continuing thereafter, has demonstrated that the combination of characteristics as herein disclosed for 'PEHY0089' are firmly fixed and are retained through successive generations of asexual reproduction.

'PEHY0089' has not been observed under all possible environmental conditions. The phenotype may vary significantly with variations in environment such as temperature, light intensity, and day length.

A Plant Breeder's Right for this cultivar has not yet been applied for. 'PEHY0089' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0089' with colors being as true as possible with an illustration of this type.

Figure 1:
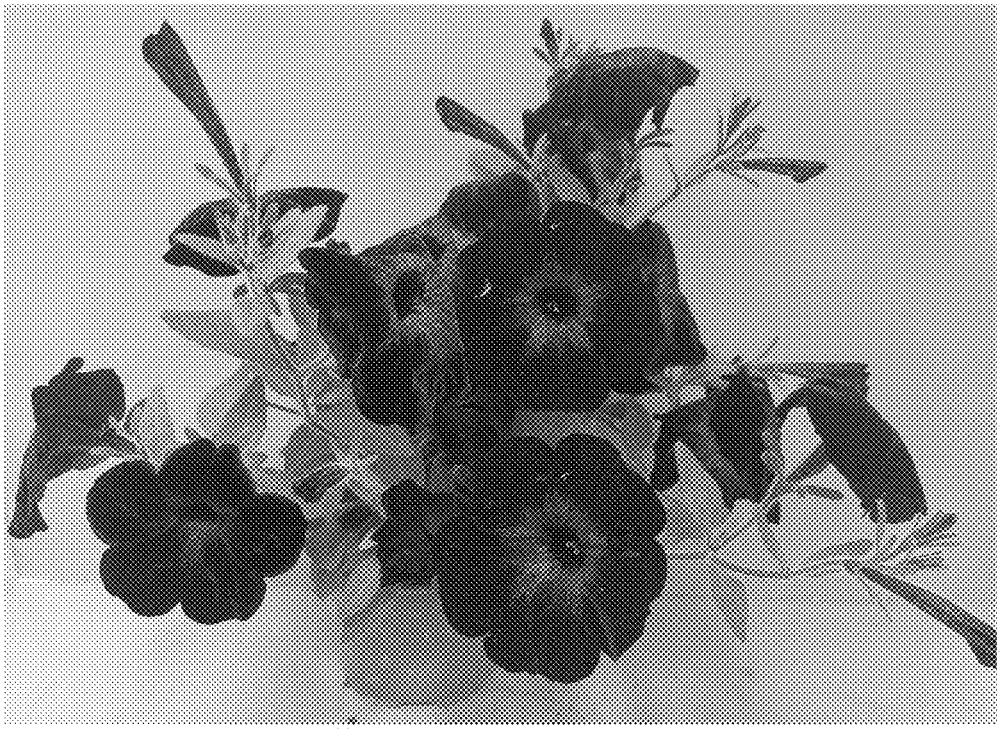
Figure 2:
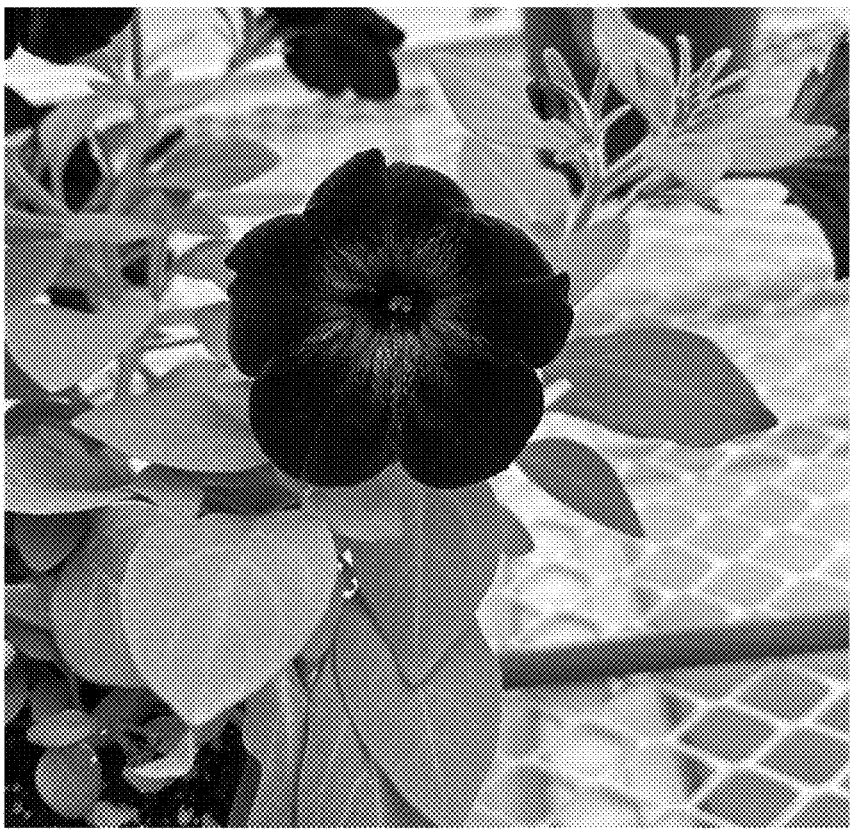

The photographic drawings show in FIG. 1 a flowering plant of the new variety and in FIG. 2 a close-up of the flowers.

DETAILED BOTANICAL DESCRIPTION

The aforementioned photographs were taken in May 2024 from plants growing indoor in 12 cm pots in Gilroy, California. These plants were approximately 12 weeks of age.

The plant descriptions and measurements were taken in April 2025 in Enkhuizen, The Netherlands on approximately 12-week-old plants that were growing in containers.

Color references are made to The Royal Horticultural Society Colour Chart (R.H.S.) 2001.

TABLE 1

DIFFERENCES BETWEEN THE NEW VARIETY 'PEHY0089' AND A SIMILAR VARIETY

| | 'PEHY0089' | 'Cascadias Indian Summer' (not patented) |
|---|---|---|
| Plant vigor: | Medium, under optimal conditions 8% increase in plant size per week. | Strong, under optimal conditions 10% increase in plant size per week. |
| Flower color: | Deep black | Yellow, bright red color |
| Plant habit: | Mounding | Trailing |

Plant:

*Form, growth and habit.*—Mounding plant habit.
*Plant height.*—20 cm.
*Plant height (inflorescence included).*—22 cm.
*Plant diameter (width).*—Approximately 26 cm.

Roots:

*Number of days to initiate and produce roots.*—16 days at about 22° C.
*Type.*—Fine, fibrous, free branching.
*Color.*—RHS N159D.

Foliage:

*Arrangement.*—Alternate, simple; sometimes opposite, decussate.
*Immature leaf, color upper surface.*—RHS 138C.
*Immature leaf, color lower surface.*—RHS 138D.
*Mature leaf, color upper surface.*—RHS 138A.
*Mature leaf, color lower surface.*—RHS 138C.
*Length.*—3.2-4.6 cm.
*Width.*—1.4-2.0 cm.
*Shape.*—Ovate.
*Base shape.*—Shortly Attenuate.
*Apex shape.*—Acute.
*Margin.*—Entire.
*Texture, upper surface.*—Densely covered with short hair.
*Lower surface.*—Densely covered with short hairs.
*Color of veins, upper surface.*—RHS 145A.
*Color of veins, lower surface.*—RHS 145A.
*Petiole color.*—RHS 145A.
*Length.*—0.5 cm.
*Diameter.*—0.3 cm.
*Petiole texture.*—Densely covered with short hairs.

Stem:

*Quantity of main branches per plant.*—4-5.
*Color of stem.*—RHS 143A.
*Length of stem.*—18 cm.
*Diameter.*—0.3 cm.
*Length of internodes.*—1.4-3.2 cm.
*Texture.*—Dense, mostly glandular short hairs.
*Color of pedicel.*—RHS 144A.
*Length of pedicel.*—2.1 cm.
*Diameter of pedicel.*—0.4 cm.
*Texture of pedicel.*—Densely covered with short hairs.

Inflorescence:

*Type.*—Flowers solitary in upper leaf axis.
*Floret type.*—Funnel-shaped; 5 lobed petals; fused at base.
*Blooming habit.*—Medium early flowering in greenhouse, flowering throughout the summer months.
*Quantity of inflorescences per plant.*—Approximately 40.
*Lastingness of individual blooms on the plant.*—About 7 days.
*Fragrance.*—Very little to no scented flowers.

Bud (just when opening):

*Color.*—RHS 201A, RHS 202B towards top.
*Length.*—3.0 cm.
*Width.*—0.6 cm.
*Shape.*—Oblong.

Immature inflorescence:

*Flower horizontal diameter.*—1.7 cm.
*Color petals, upper surface.*—RHS 202B, RHS 202A towards margin.
*Color petals, lower surface.*—RHS 202B, RHS 202A towards margin veins RHS 187A.

Mature flower:

*Flower horizontal diameter.*—5.8 cm.
*Flower height (vertical).*—2.5-3.5 cm.
*Color upper surface.*—RHS 202B, RHS 202A towards margin.
*Color lower surface.*—RHS 187A.
*Conspicuousness of veins.*—Weak to medium.
*Apex shape.*—Acuminate.
*Margin.*—Entire.
*Waviness of margin.*—Medium.
*Petal lobation.*—Medium.
*Petal texture, upper surface.*—Smooth.
*Petal texture, lower surface.*—Smooth, occasionally a short hair.
*Corolla tube color outside.*—RHS 202B.
*Corolla tube color inside.*—RHS 202A.
*Conspicuousness of veins in tube.*—Medium.
*Corolla tube length.*—2.7 cm.
*Corolla tube texture, outside.*—Rather dense and short glandular hairs.
*Corolla tube texture, inside.*—Glabrous.

Calyx:

*Color of sepal, upper surface.*—RHS 137B.
*Color of sepal, lower surface.*—RHS 137C.
*Length.*—1.8 cm.
*Width.*—0.3 cm.
*Shape.*—Ensiform.
*Apex shape.*—Acute.
*Base.*—Fused.
*Margins.*—Entire.
*Texture, upper surface.*—Densely covered with short glandular hairs.
*Lower surface.*—Densely covered with short glandular hairs.

Reproductive organs:

*Pistil.*—1.
*Length.*—2.2 cm.
*Style color.*—RHS 144B.
*Style length.*—1.5 cm.
*Stigma color.*—RHS 143B.
*Stamens.*—
*Quantity per flower* 5.
*Color of filaments.*—RHS 142D.
*Length filaments.*—1.2 cm.
*Anther color.*—RHS 202D.
*Anther length.*—0.3 cm.
*Anther shape.*—Elliptical.

*Color of pollen*.—RHS 188C.
*Pollen amount*.—Medium.
*Fertility/seed set*.—Has not been observed on this hybrid.
*Disease/pest resistance*.—Has not been observed on this hybrid.

What is claimed is:

1. A new and distinct variety of *Petunia* plant named 'PEHY0089' substantially as illustrated and described herein.

* * * * *